378/53

United States Patent [19]
Ohtsuchi et al.

[11] Patent Number: 5,247,559
[45] Date of Patent: Sep. 21, 1993

[54] SUBSTANCE QUANTITATIVE ANALYSIS METHOD

[75] Inventors: Tetsuro Ohtsuchi, Osaka; Hiroshi Tsutsui, Yawata, both of Japan

[73] Assignee: Matsushita Electric Industrial Co., Ltd., Osaka, Japan

[21] Appl. No.: 956,257

[22] Filed: Oct. 5, 1992

[30] Foreign Application Priority Data

Oct. 4, 1991 [JP] Japan ............................. 3-257396
Dec. 18, 1991 [JP] Japan ............................. 3-333794

[51] Int. Cl.$^5$ ............................................ G01N 23/06
[52] U.S. Cl. ...................................... 378/53; 378/54; 378/56
[58] Field of Search ................... 378/57, 53, 54, 56, 378/57, 62

[56] References Cited

U.S. PATENT DOCUMENTS

| | | |
|---|---|---|
| 3,848,130 | 11/1974 | Macovski . |
| 4,029,963 | 6/1977 | Alvarez et al. . |
| 4,455,669 | 6/1984 | Aichinger et al. . |
| 4,626,688 | 12/1986 | Barnes . |
| 4,811,373 | 3/1989 | Stein . |
| 4,947,414 | 8/1990 | Stein . |
| 4,953,192 | 8/1990 | Plewes . |
| 4,980,904 | 12/1990 | Sones et al. . |
| 5,033,075 | 7/1991 | DeMone et al. . |
| 5,040,199 | 8/1991 | Stein . |
| 5,177,776 | 1/1993 | Ohmori et al. .................. 378/54 |

FOREIGN PATENT DOCUMENTS

| | | |
|---|---|---|
| 0168090 | 1/1986 | European Pat. Off. . |
| 2477826 | 9/1981 | France . |
| 3-286743 | 12/1991 | Japan . |
| 1385049 | 3/1988 | U.S.S.R. ....................... 378/53 |
| 2083908 | 3/1982 | United Kingdom .............. 378/53 |
| 2088050 | 6/1982 | United Kingdom .............. 378/53 |

OTHER PUBLICATIONS

Coleman et al. "A Beam-Hardening Correction Using Dual-Energy Computed Tomography", *Phys. Med. Biol.*, 1985, vol. 30, No. 11, 1251-1256.
Stonestrom et al. "A Framework for Spectral Artifact Correcetions in X-Ray CT", *IEEE Transactions on Biomedical Eng.*, vol. BME-28, No. 2, Feb. 1981.

Primary Examiner—David P. Porta
Attorney, Agent, or Firm—Wenderoth, Lind & Ponack

[57] ABSTRACT

Radiation transmission intensity information obtained from a radiation source of two different energy levels or energy bands is used to perform an energy subtraction calculation and quantify the constituent substances of the object being analyzed. The objective is to simultaneously detect and quantify the plural substances composing the object being analyzed in a single operation using a single subtraction calculation equation. An energy subtraction calculation is first performed to eliminate a specific substance in the object being analyzed, making it possible to simultaneously determine the other two constituent substances using the negativity of the calculated result. When three substances are overlapping in the direction of radiation transmission, using the transmission intensity information from a radiation source with only two energy levels, the effect of one substance is eliminated while identifying and quantifying the other two by applying an energy subtraction calculation process that eliminates the first substance and obtains the density of a third substance, and obtains the density of the third substance in an area where the three substances overlap based on the calculated result for the area containing the first and second substances.

9 Claims, 12 Drawing Sheets

SUBSTANCE QUANTITATIVE ANALYSIS METHOD

FIELD OF THE INVENTION

The present invention relates to a method for substance quantitative analysis using radiation, and particularly to a body composition analysis method using a bone densitometry.

BACKGROUND OF THE INVENTION

The energy subtraction method which uses the transmission intensity of a radiation source containing plural energy levels or energy bands is a conventional method of determining the quantity of specific substances in a physical object.

When the object being analyzed is composed of two different substances, the quantity of a specific constituent substance can be determined as follows. By way of example, an object 80 composed of substances identified simply as substance A and substance C as shown in FIG. 12 is to be analyzed.

Because the energy subtraction method is used, radiation 4 comprising two different energy levels E1 and E2 is irradiated to the object 80 being analyzed, and the corresponding transmission intensities values $I_1$ and $I_2$ are measured at predetermined points.

The transmission intensities $I_{X1}$ and $I_{X2}$ of the radiation 4 comprising two different energies E1 and E2 passing through the object 80 at point X in FIG. 12 can be expressed by equations 1 and 2 below.

$$I_{X1} = I_{01} \exp(-\mu_{A1}\rho_A T_A - \mu_{C1}\rho_C T_C') \quad [1]$$

$$I_{X2} = I_{02} \exp(-\mu_{A2}\rho_A T_A - \mu_{C2}\rho_C T_C') \quad [2]$$

The transmission intensities $I_{Y1}$ and $I_{Y2}$ after passing through the object 80 at point Y in FIG. 12 can be expressed by equations 3 and 4 below.

$$I_{Y1} = I_{01} \exp(-\mu_{C1}\rho_C T_C) \quad [3]$$

$$I_{Y2} = I_{02} \exp(-\mu_{C2}\rho_C T_C) \quad [4]$$

In each of the equations above, $\mu_{A1}$, $\mu_{A2}$, $\mu_{C1}$, and $\mu_{C2}$ are the mass attenuation coefficients of substances A and C at energy levels E1 and E2; $I_{01}$ and $I_{02}$ are the radiation intensities of the energy levels E1 and E2 irradiated to the object 80, respectively; $\rho_A$ and $\rho_C$ are the density of substances A and C, respectively; $T_A$ and $T_C$ are the thicknesses of substances A and C, respectively. $T_C'$ is the thickness of substance C at X as defined by equation [5].

$$T_C' = T_C - T_A \quad [5]$$

The density of substance A is obtained based on the energy subtraction calculation equation [6], which eliminates the effect of $T_C$.

$$S = R_C \cdot \ln(I_2/I_{02}) - \ln(I_1/I_{01}) \quad [6]$$

where $R_C = \mu_{C1}/\mu_{C2}$.

Because the transmission intensities at point X are expressed by equations 1 and 2, the result of equation 6 is as shown by equation 7.

$$S = R_C \cdot \ln(I_{A2}/I_{02}) - \ln(I_{A1}/I_{01}) \quad [7]$$

$$= (\mu_{A1} - \mu_{A2}R_C)\rho_A T_A$$

The density $m_A$ per unit area of substance A can thus be obtained by equation 8.

$$m_A = \rho_A T_A = \frac{S}{\mu_{A1} - \mu_{A2}R_C} \quad [8]$$

$$= \frac{R_C \cdot \ln(I_{A2}/I_{02}) - \ln(I_{A1}/I_{01})}{\mu_{A1} - \mu_{A2}R_C}$$

Because the transmission intensities at point Y are expressed by equations [3] and [4], calculating equation [6] for the value of S results in 0 (zero). It is therefore possible to identify the presence of substance A at each point of the object 80 using the subtraction calculation shown in equation [6], and the density can be quantified. By processing the resulting data, it is also possible to obtain an image showing the density of substance A relative to the other constituent substances.

When a third substance B 12 is also present in the object 10 being analyzed as shown in FIG. 1, it is now necessary obtain the density $m_B$ per unit area of this substance B 12 by calculating equations similar as those [7] and [8].

When the object being analyzed is composed of three types of substances in a layered construction whereby the radiation passes through all three substances, it is necessary to use a radiation source with three energy bands.

The process whereby an object 20 comprising three different substances A 21, B 22 and C 23, as shown in FIG. 2, is described next.

Because the energy subtraction method is used, a radiation 4 comprising three different energy bands E1, E2, and E3 is irradiated to the object 20 being analyzed.

The transmission intensities values $I_{aa1}$, $I_{aa2}$, and $I_{aa3}$ of the radiation 4 comprising three different energy bands E1, E2, and E3 passing through the object 80 at point aa in FIG. 2 can be expressed by equations 9, 10, and 11 below.

$$I_{aa1} = I_{01}\exp(-\mu_{A1}\rho_A T_A - \mu_{B1}\rho_B T_B - \mu_{C1}\rho_C T_C') \quad [9]$$

$$I_{aa2} = I_{02}\exp(-\mu_{A2}\rho_A T_A - \mu_{B2}\rho_B T_B - \mu_{C2}\rho_C T_C') \quad [10]$$

$$I_{aa3} = I_{03}\exp(-\mu_{A3}\rho_A T_A - \mu_{B3}\rho_B T_B - \mu_{C3}\rho_C T_C') \quad [11]$$

The transmission intensities $I_{cc1}$, $I_{cc2}$ and $I_{cc3}$ after passing through the object at point cc in FIG. 2 can be expressed by equations 12, 13 and 14 below.

$$I_{cc1} = I_{01}\exp(-\mu_{C1}\rho_C T_C) \quad [12]$$

$$I_{cc2} = I_{02}\exp(-\mu_{C2}\rho_C T_C) \quad [13]$$

$$I_{cc3} = I_{03}\exp(-\mu_{C3}\rho_C T_C) \quad [14]$$

The transmission intensities $I_{bb1}$, $I_{bb2}$ and $I_{bb3}$ after passing through the object at point bb in FIG. 2 can be expressed by equations 15, 16 and 17 below.

$$I_{bb1} = I_{01}\exp(-\mu_{B1}\rho_B T_B - \mu_{C1}\rho_C T_C'') \quad [15]$$

$$I_{bb2} = I_{02}\exp(-\mu_{B2}\rho_B T_B - \mu_{C2}\rho_C T_C'') \quad [16]$$

$$I_{bb3} = I_{03}\exp(-\mu_{B3}\rho_B T_B - \mu_{C3}\rho_C T_C'') \quad [17]$$

In each of the equations 9-17 above, $\mu_{A1}, \mu_{A2}, \mu_{A3}, \mu_{B1}, \mu_{B2}, \mu_{B3}, \mu_{C1}, \mu_{C2}$ and $\mu_{C3}$ are the mass attenuation coefficients of substances A, B, and C at energy bands E1, E2 and E3, respectively; $I_{01}, I_{02}$ and $I_{03}$ are the radiation intensities of the energy bands E1, E2, E3, respectively, irradiated to the object; $\rho_A$, $\rho_B$ and $\rho_C$ are the densities of substances A, B and C, respectively; and $T_A$, $T_B$ and $T_C$ are the thickness of substances A, B, and C, respectively. $T_C'$ and $T_C''$ are defined by equations 18 and 19 below.

$$T_C' = T_C - T_A - T_B \qquad [18]$$

$$T_C'' = T_C - T_B \qquad [19]$$

The logarithm of both sides of equations 9-11 is obtained and expressed as follows.

$$L_{aa1} = -\mu_{A1}\rho_A T_A - \mu_{B1}\rho_B T_B - \mu_{C1}\rho_C T_C' \qquad [20]$$

$$L_{aa2} = -\mu_{A2}\rho_A T_A - \mu_{B2}\rho_B T_B - \mu_{C2}\rho_C T_C' \qquad [21]$$

$$L_{aa3} = -\mu_{A3}\rho_A T_A - \mu_{B3}\rho_B T_B - \mu_{C3}\rho_C T_C' \qquad [22]$$

By eliminating $T_B$ and $T_C'$ from these three equations and solving for $T_A$, equation 23 is obtained.

$$m_A = \rho_A T_A = D_A/D \qquad [23]$$

where $D_A$ and $D$ are defined as $$\begin{aligned}D_A = &-\mu_{A1}\mu_{B2}\mu_{C3} - \mu_{B1}\mu_{C2}\mu_{A3} - \mu_{C1}\mu_{A2}\mu_{C3} \\ &+ \mu_{C1}\mu_{B2}\mu_{A3} + \mu_{A1}\mu_{C2}\mu_{B3} + \mu_{B1}\mu_{A2}\mu_{C3}\end{aligned} \qquad [24]$$

$$\begin{aligned}D = &S_1\mu_{B2}\mu_{C3} + \mu_{B1}\mu_{C2}S_3 + \mu_{C1}S_2\mu_{C3} \\ &- \mu_{C1}\mu_{B2}S_3 - S_1\mu_{C2}\mu_{B3} - \mu_{B1}S_2\mu_{C3}\end{aligned} \qquad [25]$$

Substance A 21 is not in the radiation transmission path at points cc and bb, and the transmission intensity of the radiation is expressed by equations [12]-[17]. Applying these values in equation [23], $m_A$ is 0 at points cc and bb.

The densities $m_B$ and $m_C$ per unit area of substances B 22 and C 23, respectively, are similarly obtained from equations [20]-[22].

The above method has thus been used to determine the quantities of specific substances in the object.

As described above, it is necessary to use a radiation source with as many energy bands as there are constituent substances in the object being analyzed. When X-ray radiation is used, energy separation using a k-edge filter is performed simultaneously to irradiation of an X-ray source with plural energy bands. Alternatively, the X-ray tube voltage is continuously switched to generate a series of X-ray beams of different energy bands.

When a k-edge filter is used to form plural energy bands, absorption by the k-edge filter reduces the photon number of each energy band, and the transmission image of the analyzed sample cannot be precisely measured. When the tube voltage is changed, excessive time is required for the measurement, and movement by the subject creates problems. In addition, the equations used in this conventional method must be varied for each substance analyzed. As a result, simultaneous quantification of plural substances in a single object is not possible in a single calculation process.

SUMMARY OF THE INVENTION

Therefore, an object of the present invention is to provide a method whereby measurement of plural substances in a single analysis sample is possible using a radiation source with fewer energy bands than substances in the sample, and quantitative analysis of plural substances is possible using a single calculation equation.

To achieve this object, the present invention uses the negative of the result calculated by the energy subtraction method to quantify the constituent substances. In addition, after a first substance is eliminated by the energy subtraction method, the calculated result of the second substance is defined as the new base, and a third overlapping substance is quantified by obtaining the difference between this base value and the third substance.

It is possible by means of this method to quantify plural substances with a single equation using both the positive and negative values after energy subtraction calculation.

For example, if the relationship between the atomic number or effective atomic number of the substances shown in FIG. 1 is substance A > substance C > substance B, the result of the energy subtraction calculation in equation [7] will be a negative value for that part containing substance B and a positive value for that part containing substance A. By thus evaluating the negativity of the result, the substances contained in a given part can be easily evaluated.

In addition, when three substances are layered as shown in FIG. 2, the third substance can be quantified even when overlapping the first and second substances by evaluating radiation with two energy levels or energy bands at a measurement point containing substances 1 and 2 in the direction of radiation transmission and at a measurement point containing substances 1, 2 and 3. Then, after eliminating the first substance using the energy subtraction method at the transmission intensity of each measurement point, the difference between the calculated result for the third substance and the calculated result for the second substance is obtained to quantify the third substance. In other words, it is possible to quantify another substance in the overlapping area by using as a new calculation base the result of a first energy difference operation at the same point.

BRIEF DESCRIPTION OF THE DRAWINGS

The present invention will become more fully understood from the detailed description given below and the accompanying diagrams wherein.

DESCRIPTION OF PREFERRED EMBODIMENTS

Figure 1:
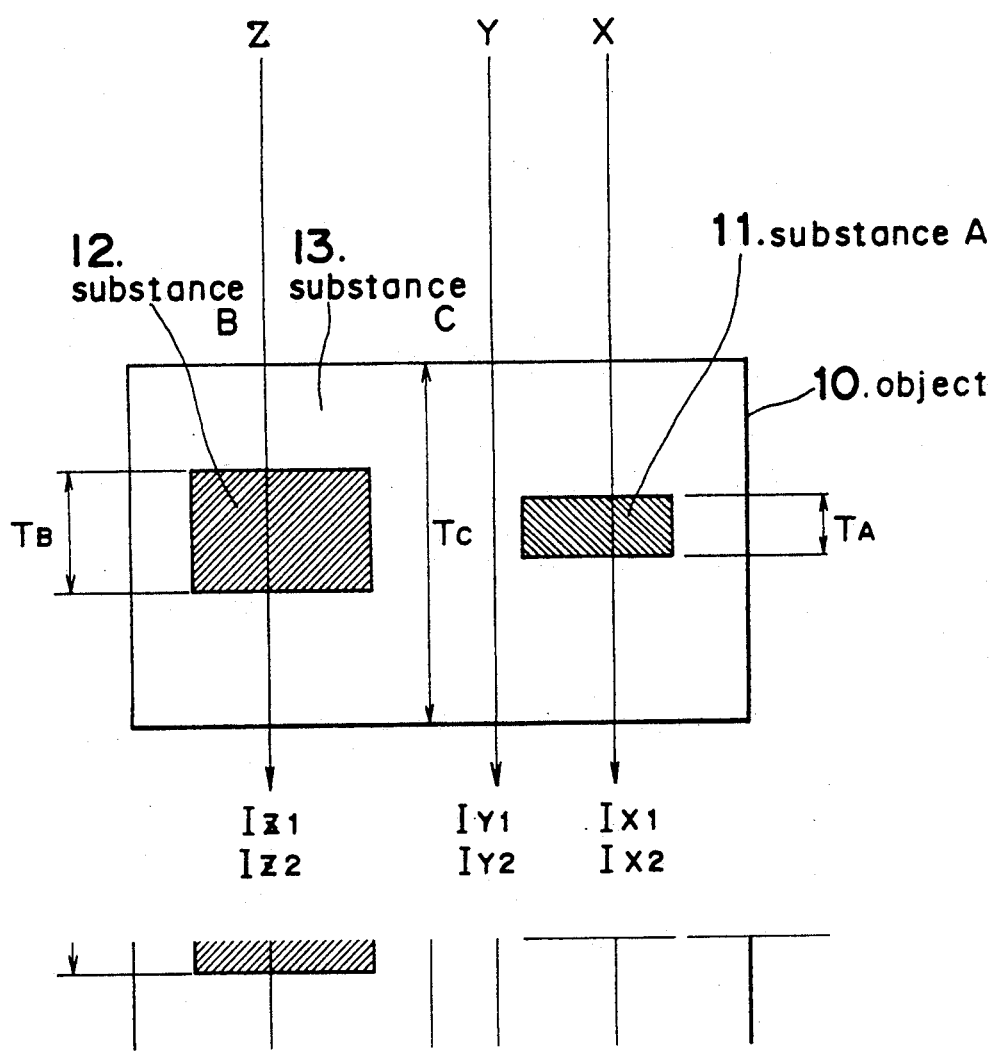
FIG. 1 is a conceptual cross section of the analyzed object used to describe the method for substance quantitative analysis according to the preferred embodiment of the invention.

The preferred embodiments of the present invention are described hereinbelow with reference to the accompanying figures. The operation of the invention with an object comprising three different substances as shown in FIG. 1 is described first.

The radiation intensity $I_1$ and $I_2$ of the transmitted energy bands E1 and E2 is calculated by applying the subtraction equation (equation [7]) for each part of the object. More specifically, the transmission intensity of the energy bands is calculated using the difference equation [7] at each part of the object believed to contain substance B 12. The transmitted radiation intensity at measurement points X and Y can be expressed by equations 1–4. The transmitted radiation intensity of part Z containing substance B 12 can be expressed as $$I_{Z1} = I_{01}\exp(-\mu_{B1}\rho_B T_B - \mu_{C1}\rho_C T_C') \quad [26]$$

$$I_{Z2} = I_{02}\exp(-\mu_{B2}\rho_B T_B - \mu_{C2}\rho_C T_C') \quad [27]$$

As a result, the values $\ln(I_{Z1}/I_{01})$ and $\ln(I_{Z2}/I_{02})$ derived from equations [26] and [27] can be substituted for the values $\ln(I_{X1}/I_{01})$ and $\ln(I_{X2}/I_{02})$ in equation [7], resulting in equation [28].

$$m_A' = \frac{\mu_{B1} - \mu_{B2}R_C}{\mu_{A1} - \mu_{A2}R_C} \rho_B T_B \quad [28]$$

When $\mu_{B1}/\mu_{B2} < R_C$ in the above equation, the difference $m_A'$ will be a negative value. The difference equation will result in a positive value for the area containing substance A because equation [7] is an energy subtraction equation used specifically to quantify this substance A 11.

It is important to note that the calculated energy difference result based on equation [7] is a negative value for those areas containing substance B 12 and a positive value for those areas containing substance A 11. The substance contained in a given area of the analyzed object can therefore easily be determined by evaluating whether the calculated result of equation [7] is positive or negative.

In general, the ratio between the low energy attenuation coefficient and the high energy attenuation coefficient increases with the increase in the effective atomic number in an energy area not containing a k absorption edge. It can therefore be concluded that a substance with an atomic number or effective atomic number greater than that of the eliminated substance (substance C 13 in this example) is found in that part of the object for which the calculated energy difference is positive, and a substance with a lower atomic number or effective atomic number is found in that part for which the calculated energy subtraction is negative.

The density $m_B$ per unit area of the substance B 12 is obtained from equation [29].

$$m_B = r_B T_B = \frac{\mu_{A1} - \mu_{A2}R_C}{\mu_{B1} - \mu_{B2}R_C} m_A' \quad [29]$$

As these equations show, it is therefore possible to obtain the density of plural substances from a single equation [7]. A practical application for this is in quantifying the amount of bone mineral content and body fat in a given part of the human body. This specific application is described next.

Figure 3:
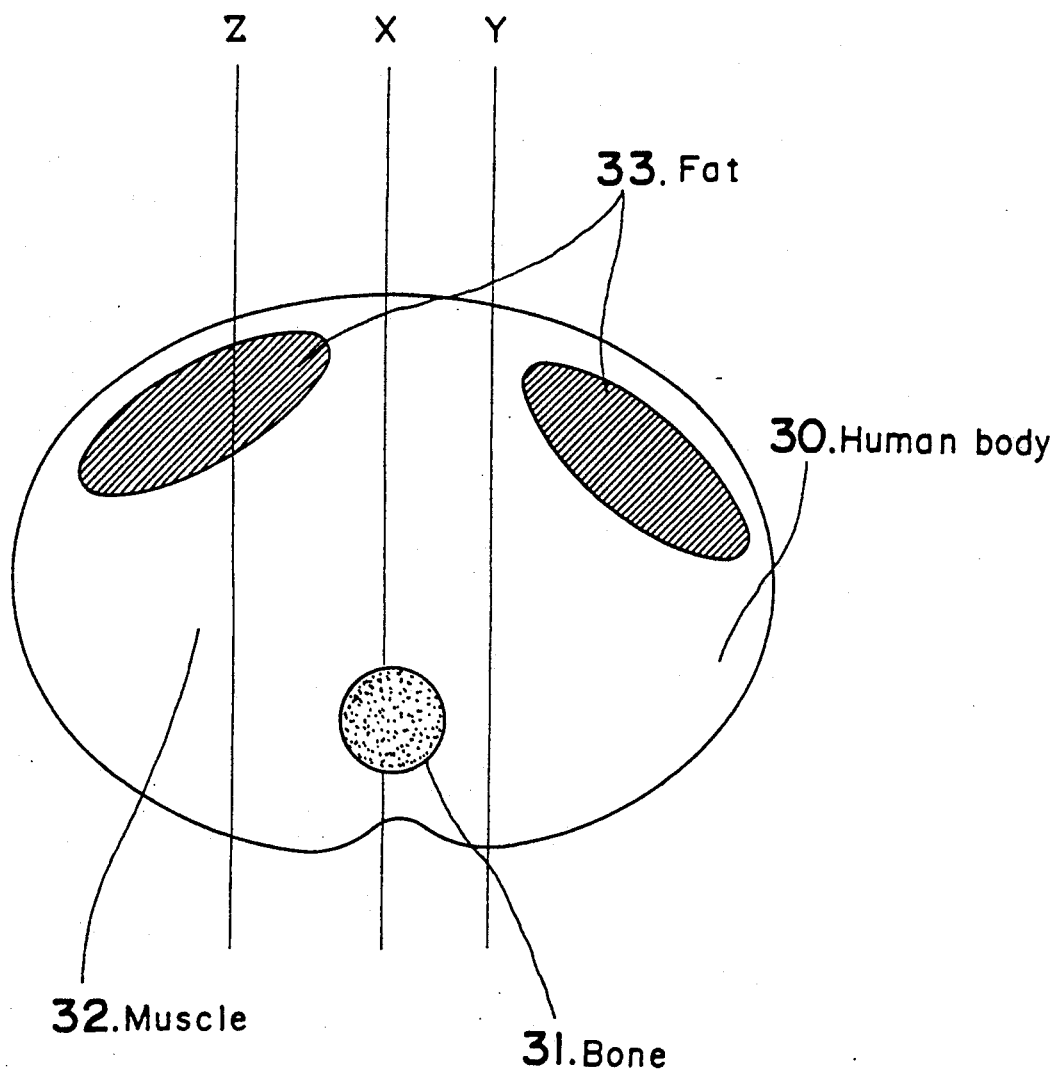
FIG. 3 is a conceptual cross section of the human hip used to describe the method for substance quantitative analysis according to the invention.
Figure 4:
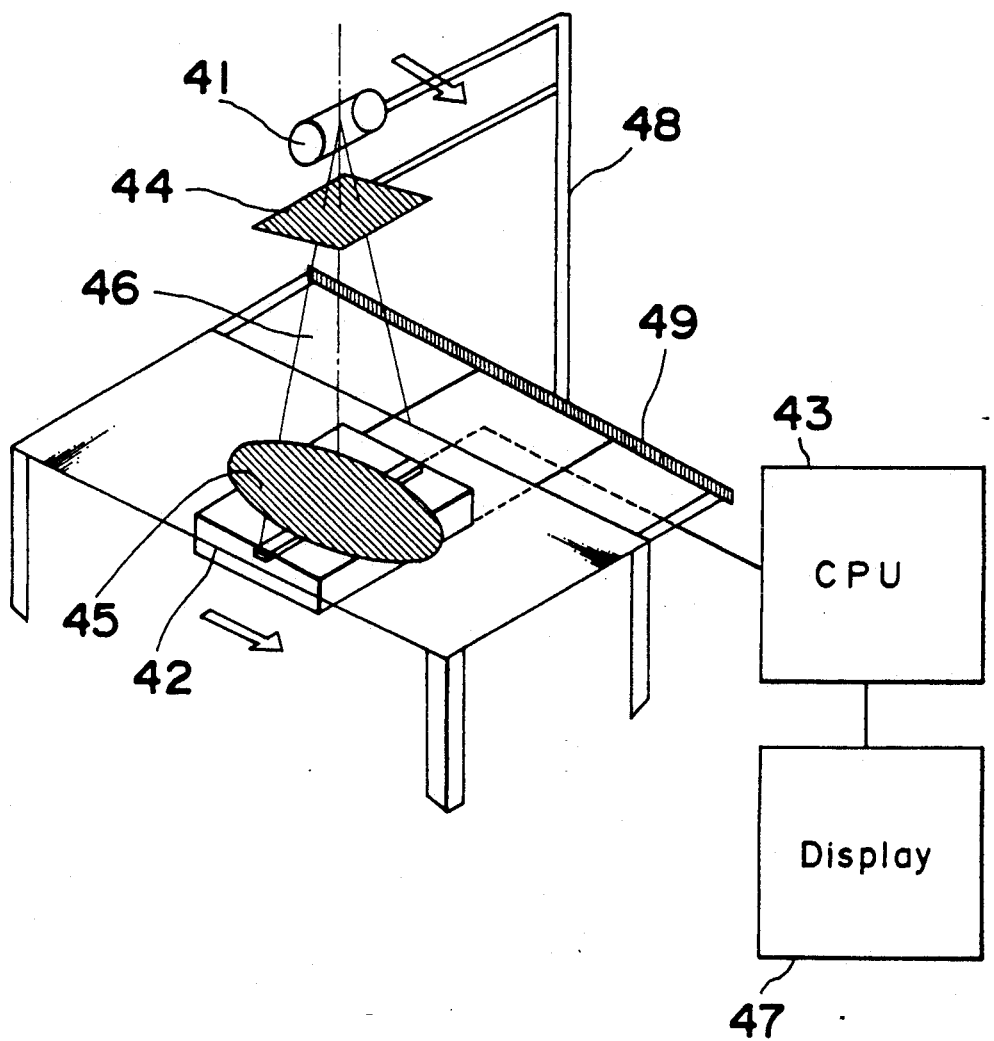
FIG. 4 is a simplified diagram of the measurement device used to achieve the method for substance quantitative analysis according to the invention.

FIG. 3 is a conceptual cross section of the human hip containing bone 31, muscle 32, and fat 33. The quantities of these tissues are measured using the X-ray transmission and measurement system shown in FIG. 4.

The primary components of this measurement system are the X-ray source 41, k-edge filter 44, X-ray image sensor 42, calculation unit 43, and image display device 47. The X-ray source 41, k-edge filter 44, and X-ray image sensor 42 are held by the support member 48, which is moved by the drive unit 49. The operation of these components is synchronized to scan the subject 45 and measure the two-dimensional transmitted radiation intensity.

Figure 5:
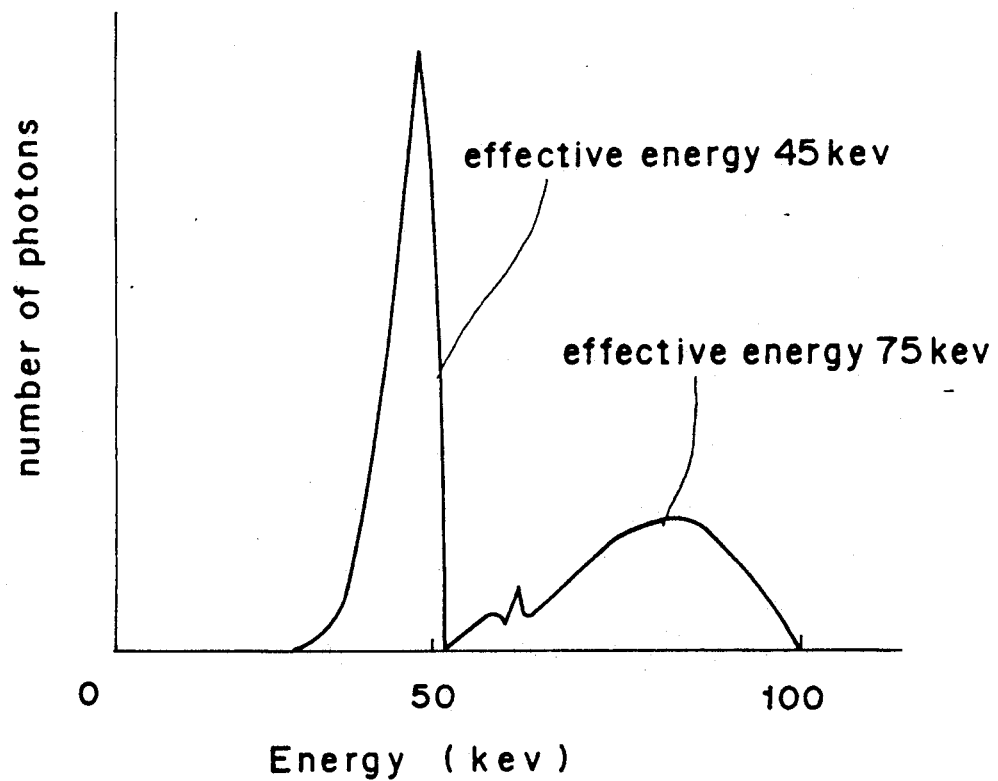
FIG. 5 is an X-ray spectrograph used in the application of the method for substance quantitative analysis according to the invention.

The k-edge filter 44 is made from gadolinium, and is provided directly below the X-ray source 41. The fan beam X-ray 46 emitted by the X-ray source 41 is separated into two energy bands by the k-edge filter 44 before irradiating the subject 45. As shown in FIG. 5, when the X-ray tube voltage is 100 kV, the effective energy is divided into two energy bands of 45 keV and 75 keV.

The X-ray image sensor 42 comprises plural detecting elements, and each detecting element can distinguish the X-ray photon energy bands. The X-ray intensity of each energy band is measured by the X-ray image sensor 42 using a photon counting method.

Figure 6:
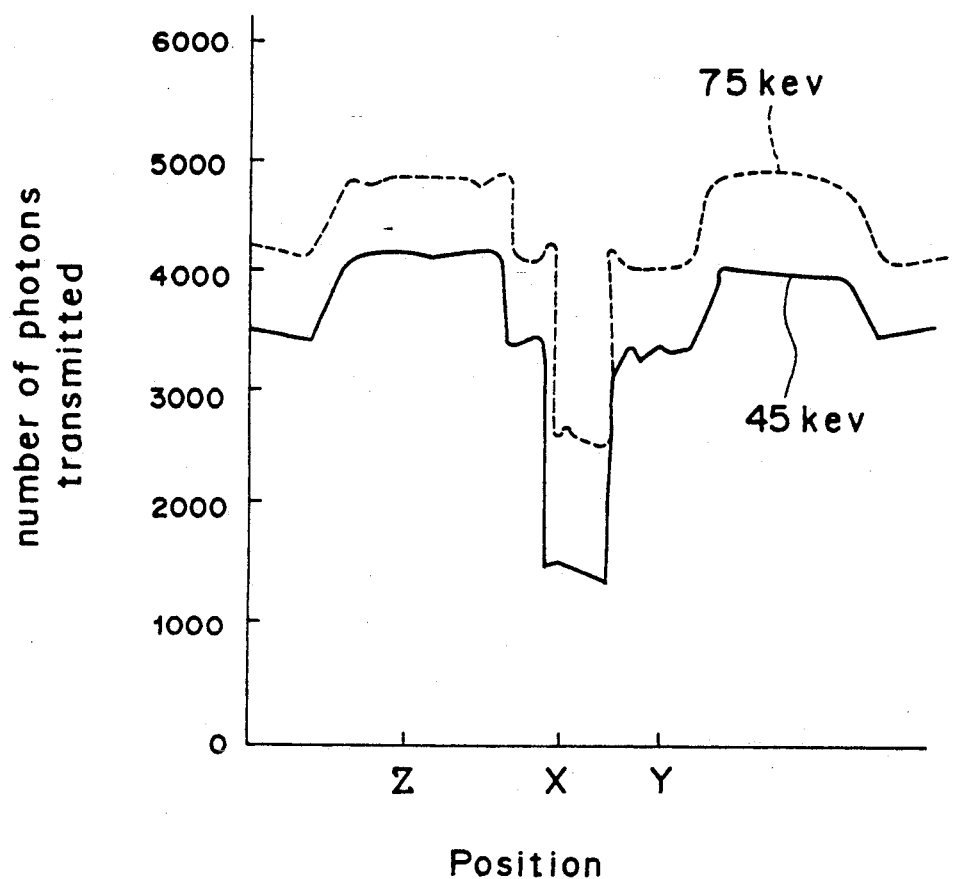
FIG. 6 is a graph of the X-ray transmission intensity measurement results in the embodiment described with reference to FIG. 3.

FIG. 6 shows the results of X-ray photon counting at each part of the subject at the two energy levels. The results obtained from the three measurement points shown in FIG. 3 are shown in Table 1. X-ray intensity was measured after passing through muscle and bone (point X), muscle only (point Y), and muscle and fat (point Z).

TABLE 1

|  | 45 keV | 75 keV |
|---|---|---|
| X (bone) | 1370 | 2770 |
| Y (muscle) | 3262 | 4100 |
| Z (fat) | 4192 | 4830 |

The energy subtraction calculation obtaining the density $m_{bone}$ per unit area of the bone was performed for all parts of the image based on the muscle value eliminated from these measurement results. In other words, substance C in equation [7] is defined as the muscle, substance A as the bone, and $m_A$ ($m_{bone}$) is calculated using the attenuation coefficients shown in Table 2.

TABLE 2

|  | 45 keV | 75 keV |
|---|---|---|
| $\mu_A$ (bone) | 0.6940 | 0.2683 |
| $\mu_C$ (muscle) | 0.2169 | 0.1763 |
| $I_O$ | 477,000 | 230,000 |
| $R_A$ | | 2.5867 |
| $R_C$ | | 1.2302 |

Figure 7:
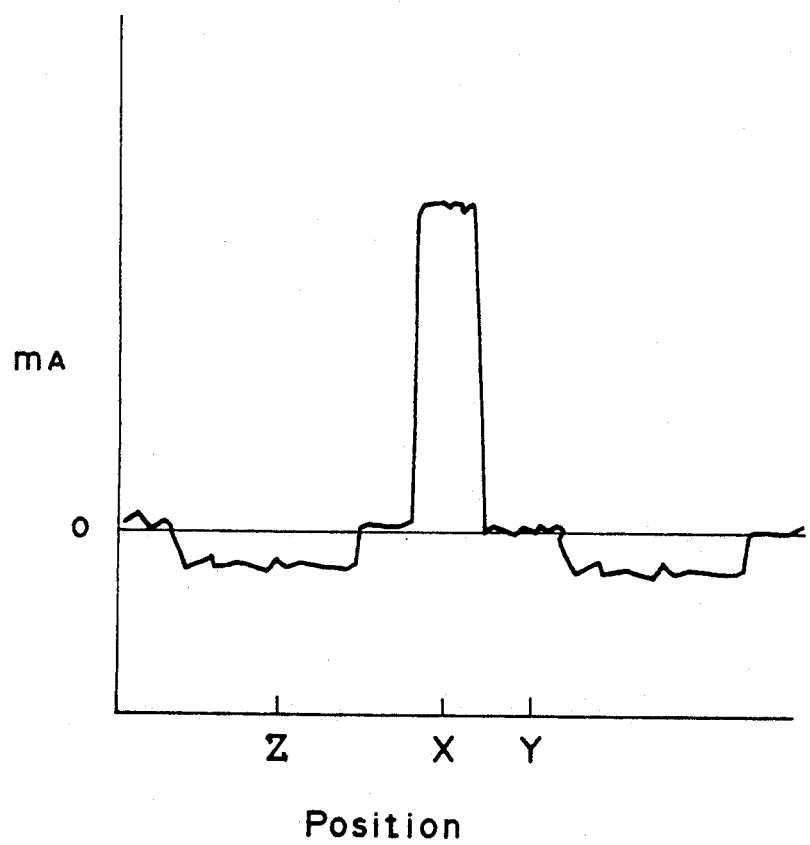
FIG. 7 is a graph of the subtraction calculation results in the embodiment described with reference to FIG. 3.

The values for $m_A$ obtained for each part from equation [7] are shown in FIG. 7 and Table 3.

TABLE 3

|  | $m_A$ |
|---|---|
| X (bone) | 1.143 |
| Y (muscle) | 0.005 |
| Z (fat) | −0.050 |

The density per unit area of bone is the positive value 1.143 g/cm$^2$, and the subtraction calculation results in a muscle value of essentially zero. Note that the value for point Z is negative. It is therefore known that a substance with an attenuation coefficient ratio less than muscle, i.e., a lower effective atomic number, is present in this area.

The numerical values of the calculated result of $m_A$ for the two-dimensional area measured by the X-ray image sensor 42 are colored for presentation on the image display device 47. Negative value areas can be readily identified by the color appearing on the image display, and the observer can immediately determine where the fat is.

The attenuation coefficient and attenuation coefficient ratio R of fat are shown in Table 4, and the effective atomic numbers of muscle, bone, and fat are shown in Table 5.

TABLE 4

|  | 45 keV | 75 keV |
|---|---|---|
| $\mu$ (fat) | 0.2135 | 0.1768 |
| R | | 1.2075 |

TABLE 5

|  | Effective atomic number |
|---|---|
| Bone | 13.8 |
| Fat | 5.92 |
| Muscle | 7.42 |

Both the attenuation coefficient ratio and effective atomic number of fat are lower than those of muscle, the reference substance. This makes it possible to determine that fat is present in those areas for which the result of the subtraction calculation is a negative value.

After the subtraction calculation is completed, the fat density per unit area is calculated by applying equation [29] to those areas for which a negative value is obtained, i.e., those areas now known to contain fat. The resulting density through point Z is 4.5529 g/cm$^2$, and the amount of fat is quantified.

In addition, by defining the areas shown as a negative value area in the image display device 47 as "areas of interest," performing the above calculations and obtaining the mean value, the fat density in the areas of interest can also be calculated.

As described hereinabove, the method of the present invention can simultaneously detect and quantify the amount of bone and fat in the body by using the negative values obtained by the subtraction calculation process.

Application of the invention to three overlapping substances is described next.

Figure 2:
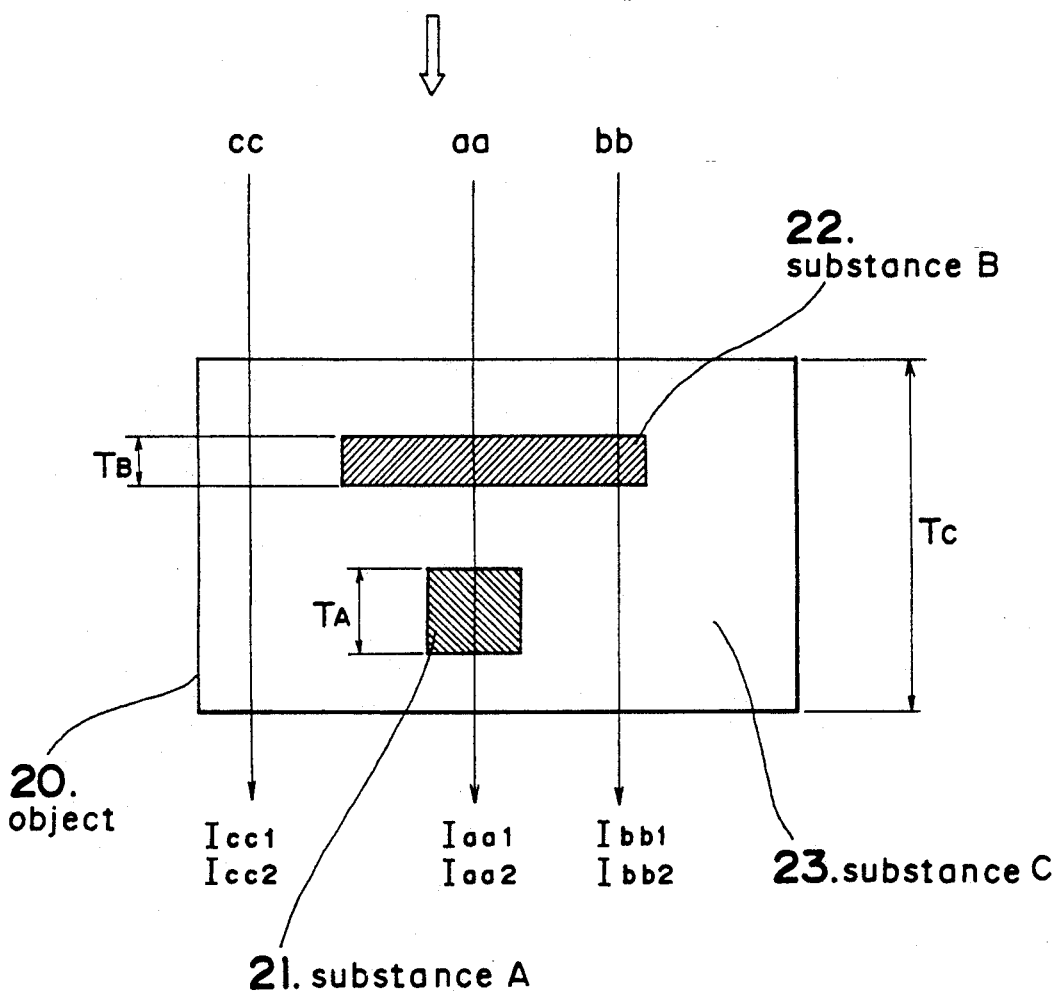
FIG. 2 is a conceptual cross section of the analyzed object used to describe the method for substance quantitative analysis according to an alternative embodiment of the invention.

Referring to FIG. 2, it is assumed in this description that the object 20 being analyzed comprises three substances A 21, B 22 and C 23, that substances A 21 and B 22 are inside substance C 23, and that substance A 21 partially overlaps substance B 22. The objective is to quantify substance A 21. This is possible as follows.

The radiation 24 intensity $I_1$ and $I_2$ of the transmitted energy bands E1 and E2 passing through selected parts of the object 20 is expressed at measurement point aa, where all three substances A, B, and C are within the transmission path, by equations [30] and [31]

$$I_{aa1} = I_{01} \exp(-\mu_{A1}\rho_A T_A - \mu_{B1}\rho_B T_B - \mu_{C1}\rho_C T_C'') \quad [30]$$

$$I_{aa2} = I_{02} \exp(-\mu_{A2}\rho_A T_A - \mu_{B2}\rho_B T_B - \mu_{C2}\rho_C T_C'') \quad [31]$$

where $T_C''$ is defined by equation [32], $$T_C'' = T_C - T_A - T_B \quad [32]$$

and at points cc and bb by equations [33] and [34], and [35] and [36], respectively, $$I_{cc1} = I_{01} \exp(-\mu_{C1}\rho_C T_C) \quad [33]$$

$$I_{cc2} = I_{02} \exp(-\mu_{C2}\rho_C T_C) \quad [34]$$

$$I_{bb1} = I_{01} \exp(-\mu_{B1}\rho_B T_B - \mu_{C1}\rho_C T_C''') \quad [35]$$

$$I_{bb2} = I_{02} \exp(-\mu_{B2}\rho_B T_B - \mu_{C2}\rho_C T_C''') \quad [36]$$

where $T_C'''$, is defined by equation [37].

$$T_C''' = T_C - T_B \quad [37]$$

By applying the energy subtraction equation [6] to each measurement point and dividing by the constant used to obtain the density of substance A 1 as in equation [8], the density at point aa and at point bb can be obtained by equations [38] and [39].

$$m_A = \frac{S}{\mu_{A1} - \mu_{A2}R_C} = \frac{R_C * \ln(I_{aa2}/I_{02}) - \ln(I_{aa1}/I_{01})}{\mu_{A1} - \mu_{A2}R_C} \quad [38]$$

$$= \rho_A T_A + \frac{\mu_{B1} - \mu_{B2}R_C}{\mu_{A1} - \mu_{A2}R_C} \rho_B T_B$$

$$m_A = \frac{S}{\mu_{A1} - \mu_{A2}R_C} = \frac{R_B * \ln(I_{bb2}/I_{02}) - \ln(I_{bb1}/I_{01})}{\mu_{A1} - \mu_{A2}R_C} \quad [39]$$

$$= \frac{\mu_{B1} - \mu_{B2}R_C}{\mu_{A1} - \mu_{A2}R_C} \rho_B T_B$$

Figure 8:
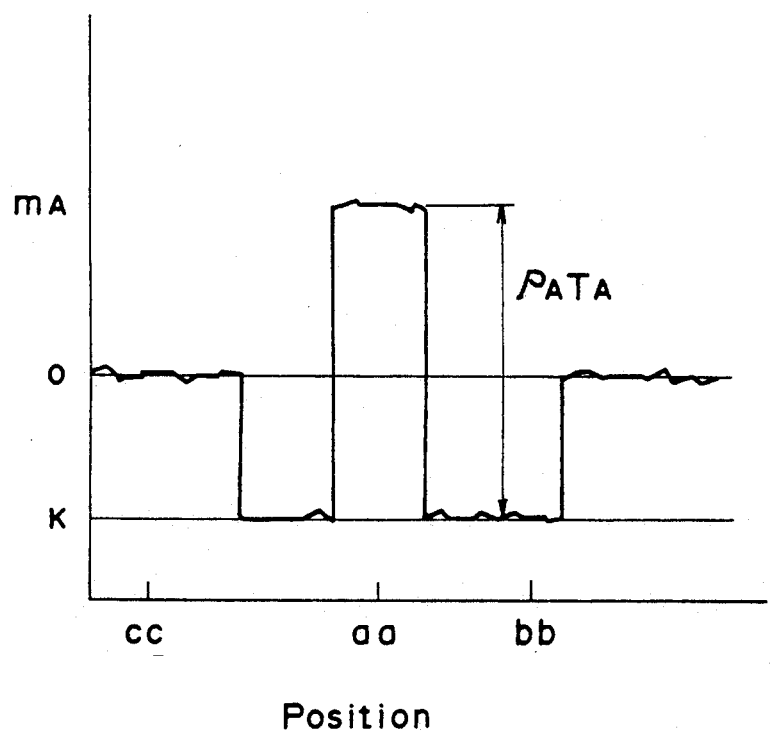
FIG. 8 is a graph of the subtraction calculation results in the analytical object shown in FIG. 2.

The calculated results of $m_A$ at each point are shown in FIG. 8. Note that $m_A = 0$ at point cc where only substance C 23 is present.

At point bb where both substance B 22 and substance C 23 are present, the result is proportional to the density per unit area of substance B 22, and the result is negative because $\mu_{B1}/\mu_{B2} < R_C$.

As shown by equation [38], the result at point aa where all three substances, A 21, B 22, and C 23, are present is equal to the sum of the density per unit area of substance A 21 added to the difference result at point bb where both substances B 22 and C 23 are present.

As a result, to obtain the value of the substance A 21 overlapping substance B 22, it is possible to obtain the difference as the density per unit area of substance A 21 based on the area where substance C 23 and substance B 22 are present. Specifically, $\rho_A T_A$ can be obtained by using k as the reference value in FIG. 8. In addition, the density of substance B can be obtained at point bb using the method described above.

As thus described, it is possible to quantify a given target substance even when this substance is found in the presence of two or more other substances. A practical application of this method to quantification of bone in the human body is described next.

Figure 9:
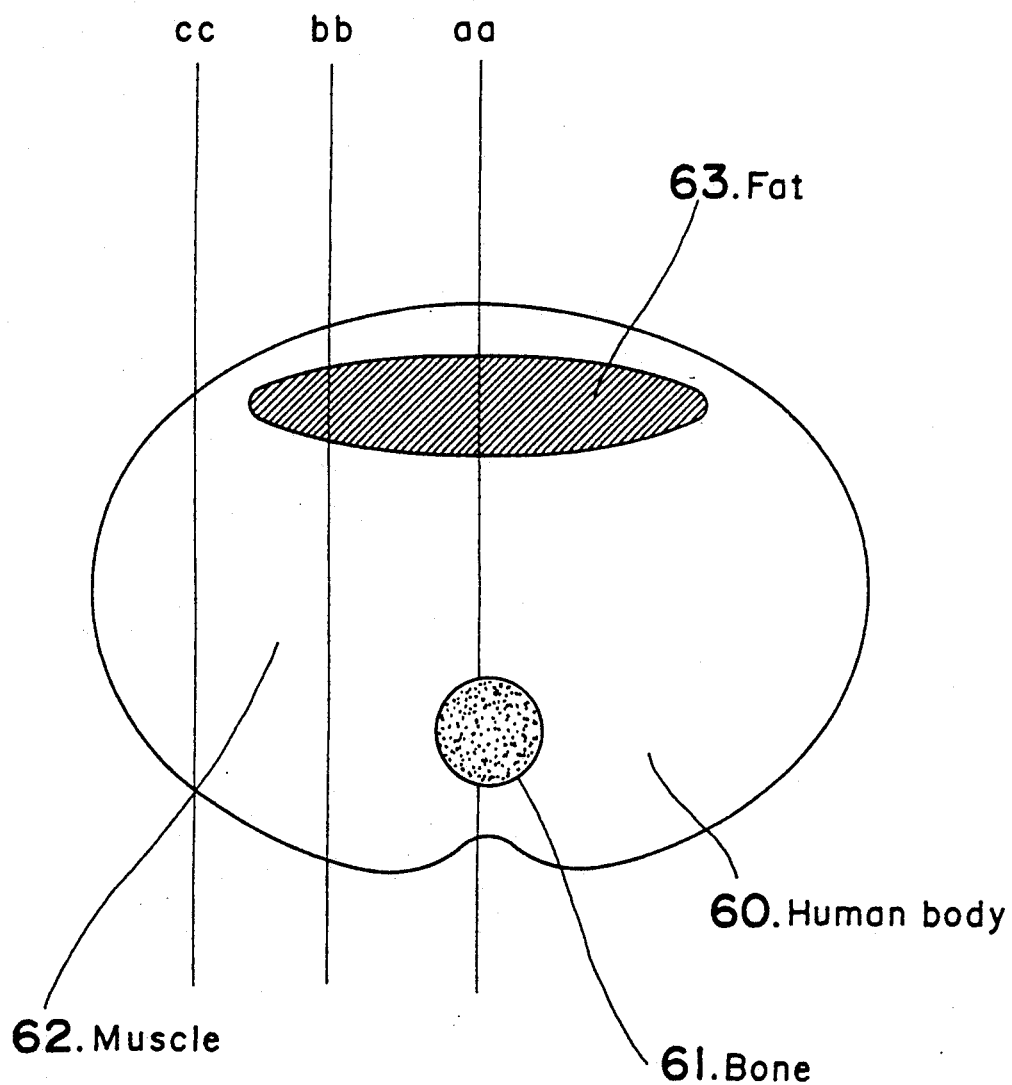
FIG. 9 is a conceptual cross section of the human hip used to describe the method for substance quantitative analysis according to an alternative embodiment of the invention.
Figure 10:
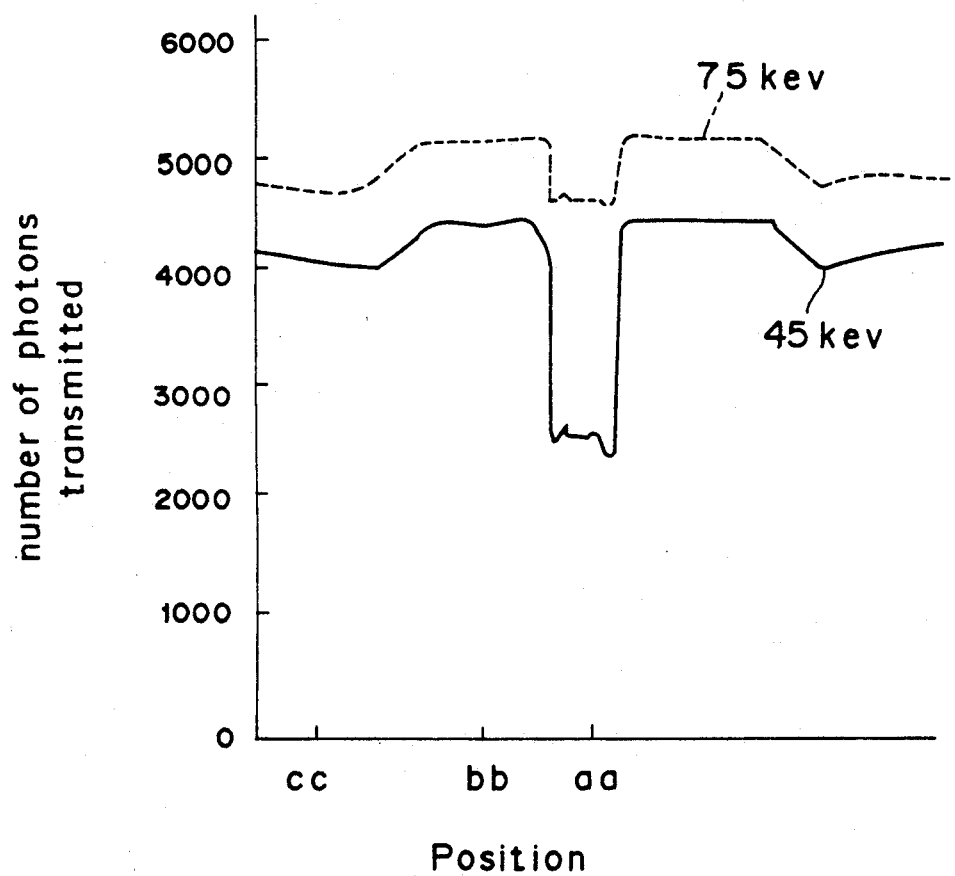
FIG. 10 is a graph of X-ray transmission intensity using the human hip in FIG. 9 as the measurement object.

FIG. 9 is another conceptual cross section of the human hip. The body 60 contains bone 61, muscle 62, and fat 63. The apparatus shown in FIG. 4 is again used to measure X-ray transmissions through the hip using 45-keV and 75-keV effective energy levels as described above. The X-ray intensity of these two energy bands is scanned and measured by the X-ray image sensor 42 using the same photon counting method as above.

For simplification, the photon count obtained for each area at each energy level is shown in Table 6 for the three measurement points in FIG. 9 only.

TABLE 6

|  | 45 keV | 75 keV |
|---|---|---|
| aa (bone) | 2776 | 4664 |
| bb (muscle) | 4773 | 5092 |
| cc (fat) | 4038 | 4756 |

The energy subtraction calculation (equation [40]) obtaining the density $m_{bone}$ per unit area of the bone was performed for all parts of the image based on the muscle value eliminated from these measurement results.

$$m_A = \frac{R_C \cdot \ln(I_{(75keV)}/I_{0(75keV)}) - \ln(I_{(45keV)}/I_{0(45keV)})}{\mu_{A(45keV)} - \mu_{A(75keV)} R_C} \quad [40]$$

The values for the attenuation coefficient of bone $\mu_A$, attenuation coefficient ratio $R_B$ of muscle, and the X-ray intensity $I_O$ used for calculation before passing through the subject are shown in Table 7.

TABLE 7

|  | $m_A$ | |
|---|---|---|
|  | 45 keV | 75 keV |
| $\mu_A$ (fat) | 0.6940 | 0.2683 |
| $I_O$ | 477,000 | 230,000 |
| $R_C$ | 1.2302 | |

Figure 11:
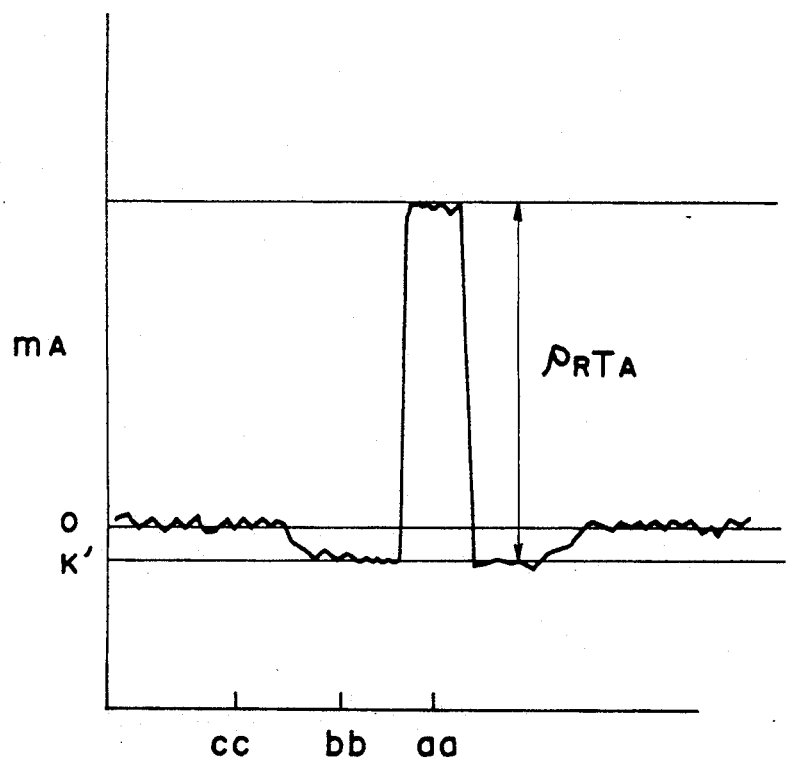
FIG. 11 is a graph of the subtraction calculation results using the human hip in FIG. 9 as the measurement object.
Figure 12:
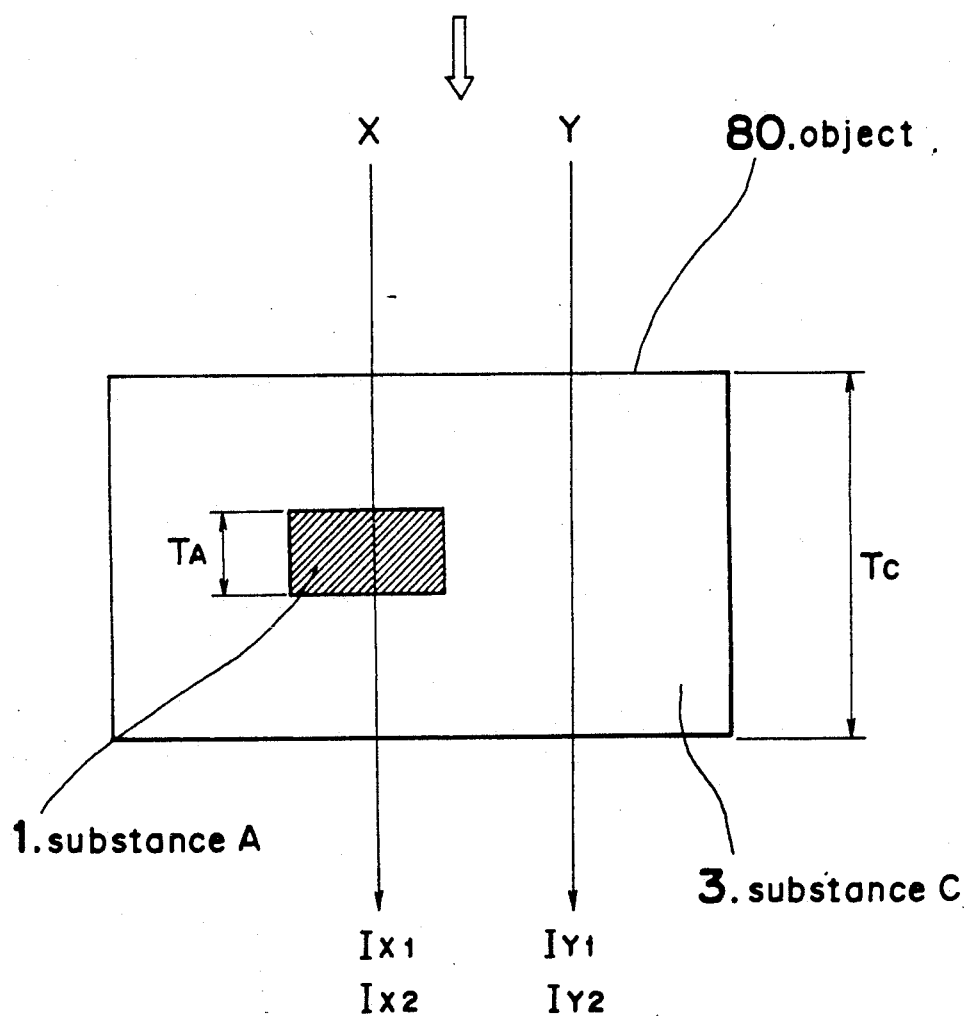
FIG. 12 is a conceptual cross section of the measurement object used to describe the conventional substance quantitative analysis method.

The graphed results of the subtraction calculation are shown in FIG. 11.

In equations [30] to [39] applied in the present embodiment, substance A is the bone, substance B is fat, and substance C is muscle. As a result, the density per unit area of bone can be obtained as the difference between the value k' at point cc (where both fat 13 and muscle 12 are present) and the measurement obtained from the bone area.

The values at points cc and aa were −0.0497 and 0.9497, respectively. The density per unit area of bone based on these values was 0.9994 g/cm².

It was also possible to obtain the density of fat at point bb using the method described above.

It is to be noted that the X-ray energy band separation method of the invention is not limited to separation using a k-edge filter as described above. It is also possible to change the X-ray tube voltage to generate X-rays at different energy levels, and measure the transmission intensity of the energy bands using an appropriate detector. It is thus possible to perform the same measurements and obtain the density of bone and fat using the same method of calculation.

As described above, it is possible by means of the method of the invention to detect and quantify the amount of bone in a given cross section of the body without fat skewing the results by selecting an appropriate reference value after the subtraction calculation process and using the difference with this reference value.

To summarize, the method of the invention provides a substance quantitative analysis method that, by using the negative component in the result of a subtraction calculation process, can simultaneously distinguish and quantify plural substances in a given object using a single equation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for substance quantitative analysis which uses radiation with two or more energy levels or bands and obtains radiation transmission information by passing the radiation through an object being analyzed,
    performs a subtraction calculation process using the obtained transmission information of the radiation with two or more energy levels or energy bands, and
    simultaneously determines or quantifies the constituent substances of the object, and
    is characterized by using the negativity of the results returned by the subtraction calculation process to eliminate a specific substance when the object is composed of three or more substances of different atomic numbers or effective atomic numbers, and simultaneously identify and quantify two or more substances by evaluating the atomic numbers or effective atomic numbers relative to the eliminated substance.

2. The method for substance quantitative analysis according to claim 1 wherein the object being analyzed is the human body, and the fat and bone in the body are determined and quantified using the negativity of the results returned by a subtraction calculation process which eliminates muscle in the body.

3. The method for substance quantitative analysis according to claim 2 wherein the measurement system used to measure the transmitted radiation intensity through the object being analyzed comprises an X-ray image sensor,
    k-edge filter, and
    x-ray source, and the transmission intensity of the plural energy level radiation beam is measured by the X-ray image sensor using a photon counting method, and quantification measurements of matter are performed using this transmission intensity information.

4. The method for substance quantitative analysis according to claim 1 wherein the measurement system used to measure the transmitted radiation intensity through the object being analyzed comprises an X-ray image sensor, k-edge filter, and X-ray source, and the transmission intensity of the plural energy level radiation beam is measured by the X-ray image sensor using a photon counting method, and quantification measurements of matter are performed using this transmission intensity information.

5. A method for substance quantitative analysis which uses radiation with two or more energy levels or energy bands and obtains radiation transmission information by passing the radiation through an object being analyzed, performs a subtraction calculation process using the obtained radiation transmission information, and simultaneously determines or quantifies the constituent substances of the object, and is characterized by applying a subtraction calculation process to eliminate a first substance at measurement points containing the first and second substances in the direction of radiation transmission, and at measurement points containing both the first and second substances and an other substance, and quantifying the other substance by defining the calculated value obtained for the second substance in these calculations as the reference value, and obtaining the difference between this reference value and the calculated value for the other substance when the object is composed of three or more substances of different atomic numbers or effective atomic numbers and these substances are overlapping in the direction of radiation transmission.

6. The method for substance quantitative analysis according to claim 5 wherein the object being analyzed is the human body, and the amount of bone in a section of the body containing muscle, bone and fat is quantified by applying a subtraction calculation process to eliminate muscle, defining the calculated result of the fat as the reference value, and obtaining the difference between the reference value and the calculated result for the bone.

7. The method for substance quantitative analysis according to claim 6 wherein the measurement system used to measure the transmitted radiation intensity through the object being analyzed comprises an X-ray image sensor, k-edge filter, and X-ray source, and the transmission intensity of the plural energy level radiation beam is measured by the X-ray image sensor using a photon counting method, and quantification measurements of matter are performed using this transmission intensity information.

8. The method for substance quantitative analysis according to claim 5 wherein the measurement system used to measure the transmitted radiation intensity through the object being analyzed comprises an X-ray image sensor, k-edge filter, and X-ray source, and the transmission intensity of the plural energy level radiation beam is measured by the X-ray image sensor using a photon counting method, and quantification measurements of matter are performed using this transmission intensity information.

9. A method for substance quantitative analysis which uses radiation with two or more energy levels or bands and obtains radiation transmission information by passing the radiation through an object being analyzed, performs a subtraction calculation process using the obtained transmission information of the radiation with two or more energy levels or energy bands, and simultaneously determines or quantifies the constituent substances of the object, and is characterized by scanning an area of an object composed of three or more substances of different atomic numbers or effective atomic numbers to obtain a two-dimensional distribution of transmission intensity regarding each energy level or band of the radiation, determining a constant so that an energy subtraction at an area where only one substance of an intermediate atomic number or effective atomic number exists along the path of the transmitting radiation may become zero, and determining the density per unit area of each of other substances by calculating an energy subtraction of each of other substances using said constant determined in the foregoing step.

* * * * *